United States Patent [19]
Pelosi, Jr. et al.

[11] 4,145,348
[45] Mar. 20, 1979

[54] 2-[[5-(4-CHLOROPHENYL)FUR-FURYLAMINO]METHYL]PYRIDINE DIHYDROCHLORIDE

[75] Inventors: Stanford S. Pelosi, Jr.; Chia-Nien Yu, both of Norwich, N.Y.

[73] Assignee: Morton-Norwich Products, Inc., Norwich, N.Y.

[21] Appl. No.: 922,861

[22] Filed: Jul. 10, 1978

[51] Int. Cl.² ............................................. C07D 491/02
[52] U.S. Cl. ....................................... 546/283; 424/263
[58] Field of Search ....................................... 260/296 R

[56] References Cited
PUBLICATIONS

Chemical Abstracts, Eighth Collective Index, (1967–1971, vols. 66–75), subject index p. 26505S, 1973.

Primary Examiner—John D. Randolph
Attorney, Agent, or Firm—Anthony J. Franze

[57] ABSTRACT

2-[[5-(4-Chlorophenyl)furfurylamino]methyl]pyridine dihydrochloride is useful as an anti-inflammatory agent.

2 Claims, No Drawings

2-[[5-(4-CHLOROPHENYL)FURFURYLAMINO]-METHYL]PYRIDINE DIHYDROCHLORIDE

This invention relates to the compound 2-[[5-(4-chlorophenyl)furfurylamino]methyl]pyridine dihydrochloride of the formula:

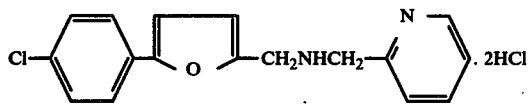

and a method for its preparation.

This compound possesses pharmacologic activity. It is particularly useful as an anti-inflammatory agent as evidenced by its ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited [Winter et al., P.S.E.B.M. 111:544(1962)].

The compound of this invention is readily prepared. Currently, it is preferred to react 5-(4-chlorophenyl)furfural with 2-aminomethylpyridine in the presence of a solvent such as methanol followed by treatment with sodium borohydride and hydrogen chloride.

In order that this invention may be fully available to and understood by those skilled in the art, the method now preferred for making it is described:

2-[[5-(4-Chlorophenyl)furfurylamino]methyl]pyridine Dihydrochloride

A mixture of 41.5 g (0.200 mole) of 5-(p-chlorophenyl)furfural, 21.7 g (0.200 mole) of 2-aminomethylpyridine in 300 ml of MeOH was heated at reflux with stirring for 3 hrs. After cooling, 7.6 g (0.20 mole) of sodium borohydride was added in 1 hr. while keeping the temperature at 25°–32°. The mixture was allowed to stir for an additional one hour and then was heated at reflux with stirring for ½ hr. After standing overnight, the solution was filtered and the filtrate was concentrated in a water bath at reduced pressure to a light brown solid. The solid was partitioned between chloroform and water. The chloroform layer was dried over $MgSO_4$ and was concentrated in a water bath at reduced pressure to a dark liquid. It was treated with 200 ml of ethanolic HCl and solid separated fairly readily. The solid was collected, washed with SDA-32, ether and air-dried. The yield was 41.5 g (56%). Recrystallization from 1 l. of ethanolic HCl gave 35 g of product, m.p. 170°–171°.

Anal. Calcd. for $C_{17}H_{15}ClN_2O.2HCl$: C, 54.93%; H, 4.61%; N, 7.54%. Found: C, 54.57%; H, 4.62%; N, 7.55%.

What is claimed is:
1. The compound 2-[[5-(4-chlorophenyl)furfurylamino]methyl]pyridine dihydrochloride.
2. The method of preparing the compound of claim 1 which consists in reacting 5-(4-chlorophenyl)furfural with 2-aminomethylpyridine followed by treatment with sodium borohydride and hydrogen chloride.

* * * * *